United States Patent [19]

Thomas

[11] Patent Number: 5,342,383
[45] Date of Patent: Aug. 30, 1994

[54] SOFT TIP OBTURATOR

[75] Inventor: Joseph J. Thomas, Berwyn, Pa.

[73] Assignee: Thomas Medical Products, Inc., Malvern, Pa.

[21] Appl. No.: 858,922

[22] Filed: Mar. 27, 1992

[51] Int. Cl.⁵ .............. A61B 17/00; A61M 5/178; A61M 25/00
[52] U.S. Cl. .................. 606/190; 606/191; 604/170; 604/282
[58] Field of Search ............... 604/57, 104, 170, 264, 604/265, 278, 280, 268, 282; 606/190, 191, 197

[56] References Cited

U.S. PATENT DOCUMENTS

| | | | |
|---|---|---|---|
| 4,637,388 | 1/1987 | Melendy | 128/207.14 |
| 4,886,506 | 12/1989 | Lovgren et al. | 604/280 |
| 4,959,067 | 9/1990 | Muller | 606/190 |
| 5,011,478 | 4/1991 | Cope | 604/165 |
| 5,045,072 | 9/1991 | Castillo et al. | 604/280 |
| 5,061,245 | 10/1991 | Waldvogel | 604/170 |
| 5,085,649 | 2/1992 | Flynn | 604/282 |
| 5,108,413 | 4/1992 | Moyers | 606/191 |
| 5,127,917 | 7/1992 | Niederhauser et al. | 606/191 |
| 5,146,925 | 9/1992 | Snow | 128/658 |

FOREIGN PATENT DOCUMENTS

| | | | |
|---|---|---|---|
| 0138089 | 4/1985 | European Pat. Off. | 606/191 |
| 3337758 | 4/1985 | Fed. Rep. of Germany | 606/191 |
| 2416687 | 10/1979 | France | 606/191 |

Primary Examiner—John D. Yasko
Assistant Examiner—Adam J. Cermak
Attorney, Agent, or Firm—Caesar, Rivise, Bernstein, Cohen & Pokotilow, Ltd.

[57] ABSTRACT

An obturator for use with a conventional sheath introducer or any other tubular member providing access to the interior of the body of a living being. The obturator comprises a shaft in the form of an elongated rod-like element having a distal end. The rod-like element is formed of a first material, e.g., polyester based polyurethane, having a first durometer, e.g., 75 (Shore D). The distal end of the rod like element is in the form of a tip formed of a second material, e.g., aliphatic polyurethane, having a second durometer, e.g., 80 (Shore A), substantially less than that of the first material. The tip is a hollow tubular body having a domed free end. The distal end of the rod-like element includes an annular recess about its periphery which cooperates with the mating shaped hollow interior surface of the tip to secure the tip in place. A radiopaque material, e.g., barium sulfate in a concentration of at least 20 percent by weight, is incorporated into the tip to facilitate radiographic location of the obturator when it is in place within the body of the being.

26 Claims, 1 Drawing Sheet

SOFT TIP OBTURATOR

BACKGROUND OF THE INVENTION

This invention relates generally to medical devices and more particularly to obturators.

Access to the vascular or other systems within the body of a living being are now being provided by many types of minimally invasive devices, such as needles, sheath introducers, catheters, etc. Often the procedure involved in providing access to the interior of the being's body requires the maintenance of the access device's lumen in position, e.g., within the interior of an artery, while providing a secure closure at the proximal fitting of the device, e.g., to prevent the egress of blood therefrom. In order to effect that secure closure, conventional devices, such as obturators, have been used in the access device's lumen. Such obturators typically comprise an elongated, rod-like element which when extended into the lumen of the access device protrude slightly beyond its distal (open) end. The obturator is held in place in the lumen via an appropriate fitting cooperating with a fitting on the access device. In order to facilitate the placement of the obturator within the access device, the obturator is typically formed of a relatively rigid material so that its tip is rigid or hard. Thus, when such a prior art obturator is used it may traumatize the tissue which is engaged by the rigid tip, particularly if the obturator is left in place (indwells) for an extended period of time.

Conventional obturators have included radiopaque materials therein, e.g., barium sulfate, in order to enable the user to radiographically image the device to determine its placement within the body. As will be appreciated by those skilled in the art the inclusion of a radiopaque material, such as barium sulfate, into an obturator material, such as polyurethane, has the effect of reducing its tensile strength (while coincidentally increasing the hardness somewhat). This factor has limited the concentration of such radiopaque materials in prior art obturators to relatively low levels, e.g., 12 percent by weight in obturators of Teflon and 20 percent by weight in obturators of polyurethane, in order to maintain structural integrity. However, by using such a relatively low concentration of radiopaque material the radiographic image produced is less than optimum.

Thus, a need exists for an obturator which does not pose a potential tissue traumatization hazard, even if left in place for an extended period of time, and whose location within the body can be readily determined utilizing radiographic imaging.

OBJECTS OF THE INVENTION

Accordingly, it is a general object of this invention to provide an obturator which overcomes disadvantages of the prior art.

It is a further object of this invention to provide an obturator having a relatively soft tip to minimize trauma to tissue engaged thereby during indwelling of the obturator.

It is still a further object of this invention to provide an obturator having a relatively soft, radiopaque tip to facilitate radiographic location.

It is yet a further object of this invention to provide an obturator having a relatively soft tip which is simple in construction.

SUMMARY OF THE INVENTION

These and other objects of this invention are achieved by providing an obturator for introduction into the body of a living being. The obturator comprises a shaft in the form of an elongated rod-like element having a distal end. The rod-like element is formed of a first material, e.g, polyurethane, having a first durometer, e.g., in the range of 50 to 75 durometer (Shore D). The distal end of the rod-like element comprises a tip formed of a second material, e.g., polyurethane, having a second durometer, e.g., in the range of 75 to 85 durometer (Shore A), substantially lower than that of the first material.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
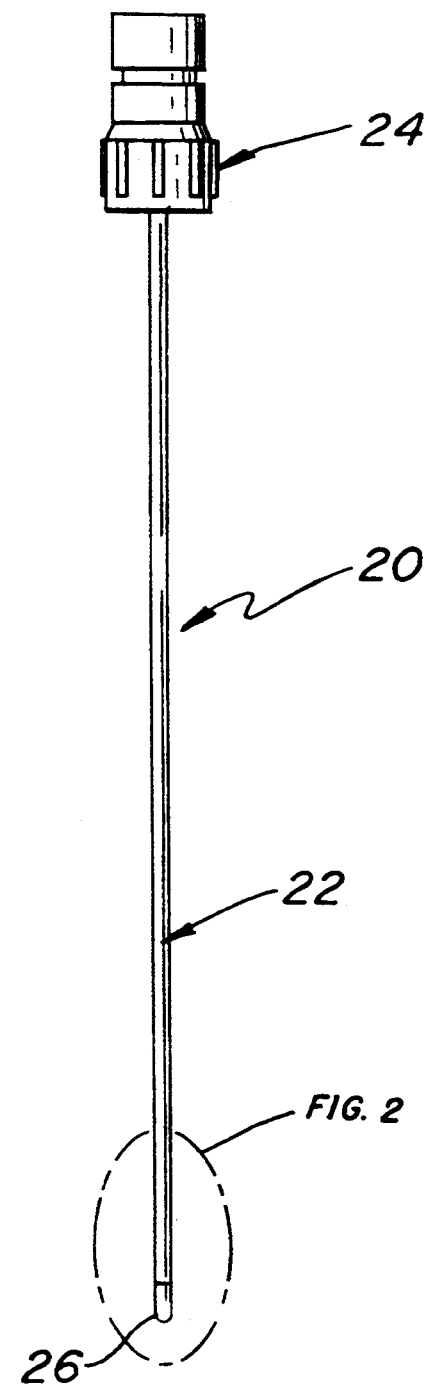
FIG. 1 is a plan view showing an obturator constructed in accordance with this invention.

Referring now to the various figures of the drawing wherein like reference characters refer to like parts, there is shown at 20 in FIG. 1, an obturator constructed in accordance with this invention. The obturator, while of a unique construction (as will be described later), never the less is of conventional shape, i.e., it consists of an elongated rod, which can be of any length or diameter so that it can be used in any conventional sheath introducer (not shown) or any other instrument having a lumen into which an obturator is to be positioned for effecting some medical procedure.

As can be seen in FIG. 1 the obturator 20 basically comprises a shaft 22 and a cap 24. The shaft 22 is in the form of an elongated rod-like element having a distal end at which a tip 26 is located. The cap 24 is of any suitable conventional construction is located at the proximal end of the shaft and is arranged to cooperate with a fitting (not shown), e.g., a sheath valve body, on the access device, e.g., introducer sheath (not shown), in which the obturator is to be located.

The rod-like element 22 can be formed of any suitable, material having a sufficiently high durometer to impart substantial rigidity to the obturator to facilitate its placement within the access device. The tip 26, however, is formed of a material, which is substantially softer, i.e., has a substantially lower durometer and molecular weight, than the material making up the rod-like element. This feature ensures that the tip does not traumatize any tissue which it engages when the obturator is in place with its distal end protruding beyond the distal end of the access device.

In accordance with a preferred embodiment of this invention the material making up the rod-like element is a polyether based polyurethane whose durometer is in the range of 55 to 75 durometer (Shore D). The tip is formed of aliphatic polyurethane, having a durometer in the range of 75 to 85 durometer (Shore A). One particularly effective polyurethane for the rod-like member is that sold by Dow Chemical Company of Midland Mich. under the trade designation Pelletbane 2363-65D, having a durometer of 65 (Shore D), while a particularly effective polyurethane for the tip is that sold by Thermedics, Inc. of Wooburn, Mass. under the trade designation Tecoflex 80A-B20, having a durometer of 80 (Shore A).

Figure 3:
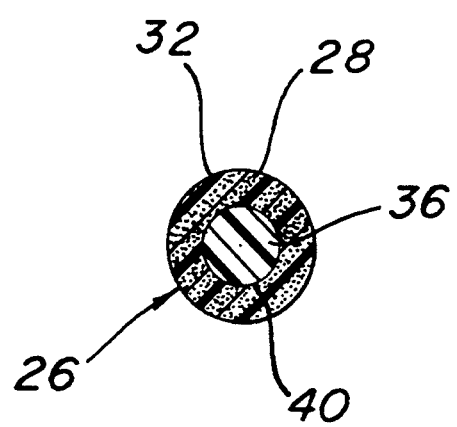
FIG. 3 is an enlarged sectional view taken along lines 3—3 of FIG. 2.

In accordance with a preferred embodiment of this invention the material making up the tip incorporates a radiopaque material 28 (FIG. 3), preferably barium sulfate, but other radiopaque materials may be used. The inclusion of the radiopaque material in the material making up the obturator tip, but not its shaft, helps to radiographically locate the obturator when it is in position within the being's body, by producing a sharply defined, distinct radiographic image. This sharply defined, distinct image is easier to locate radiographically than that produced by prior art obturators utilizing radiographic material incorporated in the full length of the obturator shaft. Moreover, the concentration of radiopaque material which can be utilized in the obturator of this invention is greater than that utilized heretofore in the prior art. This feature enables the production of an even more distinct image by the subject obturator than that produced by the prior art. In this regard since the subject invention makes use of a tip which is quite soft, and in which the radiopaque material is confined, a reduction of tensile strength (and a slight increase in hardness) of that tip caused by an increased concentration of radiopaque material therein is of no significant concern (whereas it is a major concern in the prior art as discussed above). Thus, with the subject invention the radiopaque material, e.g., barium sulfate, etc., can be mixed in with the material, e.g., polyurethane, making up the tip in a relatively high concentration, e.g, from 20 to 50 percent by weight, to increase the radiopacity and discriminatability of the tip when it is imaged.

Figure 2:
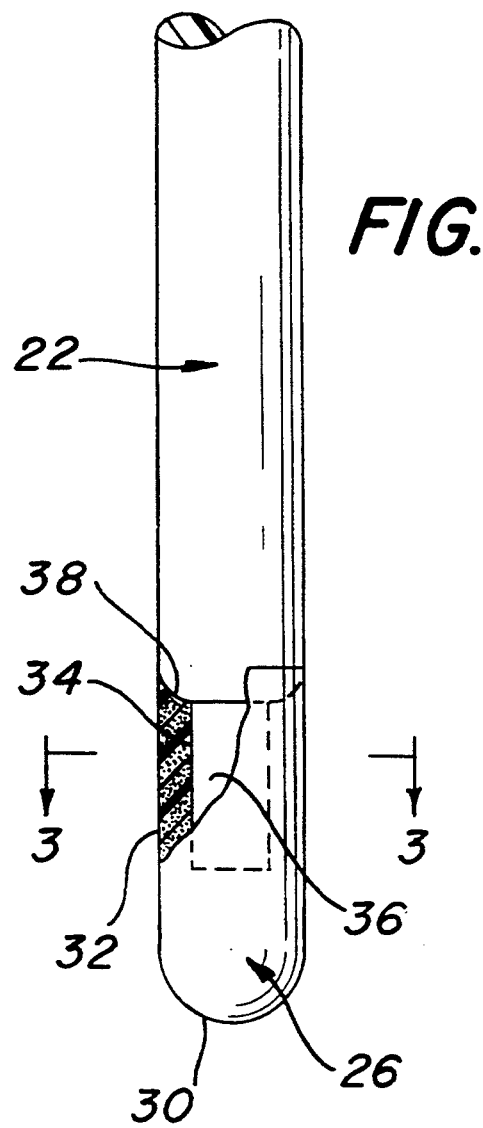
FIG. 2 is an enlarged plan view, partially in section, of the tip and contiguous portion of the obturator shown within the area designated "FIG. 2" in FIG. 1.

Referring now to FIG. 2 the structural details of the tip 26 will now be considered. As can be seen therein the tip 26 is a generally cylindrical member of the same outer diameter and profile as the rod-like element 22 and terminates in a domed distal end 30. The tip 26 can be formed and secured on the distal end of the rod-like element 22 in various ways. In accordance with a preferred embodiment the tip 26 is formed as a separate, hollow cylindrical element or sleeve 32 which is bonded, e.g., fused, to the distal end of the rod-like element by the application of heat and pressure. To that end, the distal end of the rod-like element includes an annular recess 34 extending about the periphery thereof to form a relatively short, e.g., 0.1 inch (2.5 mm), centrally located axial extension 36. The interface between the annular recess 34 and the remainder of the rod-like element is in the form of an arcuate wall 38. The cylindrical sleeve 32 which forms the tip has a hollow interior space 40 therein whose inside diameter, e.g., 0.04 inch (1 mm) is approximately the same as the outside diameter, e.g., 0.038 inch (1 mm), of the axial extension 36 of the rod-like element 22. The sleeve 32 is placed on the distal end of the rod-like element so that the extension 36 is located within the hollow space 40. Then the distal end of the rod-like element 22 with the sleeve 32 thereon is placed in a die (not shown) and subjected to heat and pressure to cause the sleeve to deform and fuse to the surfaces of the distal end of the rod-like element 22, thereby permanently securing the tip in place and at the same time forming its domed free end 30.

While the tip 26 can be of any length desired, it is preferable that its length be such that it forms only that portion of the obturator which extends beyond the free end of the access device, e.g., the introducer sheath, when the obturator is in place therein. Thus, for a obturator whose shaft is approximately 7 inches (a conventional length), the tip 26 is preferably within the range of 0.15 inch (3.8 mm) to 0.23 inch (5.8 mm) long. The outer diameter of the shaft, i.e., the rod-like element and the tip, can be of any desired size, e.g., 6 or 7 French (0.091 inch and 0.078 inch, respectively), and is preferably 1 French less than the size of the lumen of the access device into which it will be placed.

It must be pointed out at this juncture that the dimensions for the obturator as set forth above are merely exemplary, as are the materials making up the various components. Thus, for example, other materials having the same or different durometers as described heretofore can be used for either of the materials making up the rod-like element 22 and the tip 26, so long as the material making up the rod-like element is sufficiently rigid and strong for structural integrity and to facilitate its placement, while the material making up the tip is sufficiently soft to minimize the risk of engagement produced-tissue trauma.

As should be appreciated from the foregoing the obturator of the subject invention is simple in construction, is as easy to use as conventional obturators, yet due to its soft tip is gentle and non-traumatic to tissue engaged thereby. Moreover, due to the confinement of radiopaque material at a relatively high concentration within the soft tip, the obturator is easy to locate radiographically.

Without further elaboration, the foregoing will so fully illustrate my invention that others may, be applying current or future knowledge, adopt the same for use under various conditions of service.

I claim:

1. An obturator for use with an access device located within a lumen extending into the cardiovascular system of a living being, said obturator comprising a shaft in the form of an elongated solid rod-like element having a distal end, said rod-like element being formed of a first material having a first durometer, said distal end comprising a tip located thereon, said rod-like element and said tip are each the same outside diameter, said tip being of a fixed shape and being formed of a second material having a second durometer and said tip comprising radiopaque means, said second durometer being substantially lower than said first durometer, wherein when said obturator is located within said access device, said tip extends outwardly therefrom, said rod-like element of said obturator being maintainable in a desired position within said access device to provide support thereto when said access device is located within said lumen, while said tip minimizes trauma to said lumen.

2. The obturator of claim 1 wherein said first durometer is in the range of 50 to 75 durometer (Shore D).

3. The obturator of claim 2 wherein said second durometer is in the range of 75 to 85 durometer (Shore A).

4. The obturator of claim 1 wherein said second durometer is in the range of 75 to 85 durometer (Shore A).

5. The obturator of claim 1 wherein said first durometer is 65 (Shore D).

6. The obturator of claim 5 wherein said second durometer is 80 (Shore A).

7. The obturator of claim 1 wherein said second durometer is 80 (Shore A).

8. The obturator of claim 1 wherein said radiopaque means comprises barium sulfate at a concentration of at least twenty percent by weight of said second material.

9. The obturator of claim 1 wherein said distal end portion comprises securing means for holding said tip in place thereon.

10. The obturator of claim 9 wherein said securing means comprises a recess in the surface of said distal end portion, and wherein said tip comprises a hollow member formed of said second material having an interior surface portion matingly engaging said recess.

11. The obturator of claim 9 wherein said recess comprises an annular recess extending about the periphery of said distal end.

12. The obturator of claim 1 wherein said tip is of a length in the range of 0.15 inch (3.8 mm) to 0.23 inch (5.8 mm).

13. The obturator of claim 12 wherein the overall length of said shaft is approximately 7 inches (17.8 cm).

14. The obturator of claim 1 wherein said first material comprises polyurethane.

15. The obturator of claim 14 wherein said first material is polyether based polyurethane.

16. The obturator of claim 14 wherein said second material comprises polyurethane.

17. The obturator of claim 16 wherein said first material comprises polyether based polyurethane and wherein said second material comprises aliphatic polyurethane.

18. The obturator of claim 17 wherein said second material additionally comprise barium sulfate at a concentration of at least twenty percent by weight of said aliphatic polyurethane.

19. The obturator of claim 16 additionally comprising radiopaque means located within said tip.

20. The obturator of claim 19 wherein said radiopaque means comprises barium sulfate at a concentration of at least twenty percent by weight of said first material.

21. The obturator of claim 1 wherein said second material comprises polyurethane.

22. The obturator of claim 21 wherein said second material comprises aliphatic polyurethane.

23. An obturator for use within a lumen extending into the body of a living being, said obturator comprising a shaft in the form of an elongated rod-like element having a distal end, said rod-like element being formed of a first material having a first durometer, said distal end comprising a tip located thereon comprising radiopaque means located within said tip, said tip comprising a second material having a second durometer, said second durometer being substantially lower than said first durometer, and wherein said radiopaque means comprises barium sulfate at a concentration of at least twenty percent by weight of said second material.

24. An obturator for use within a lumen extending into the body of a living being, said obturator comprising a shaft having a length of approximately 7 inches (17.8 cm) and being in the form of an elongated rod-like element having a distal end, said shaft and said rod-like element having the same outside diameter, said rod-like element being formed of a first material having a first durometer, said distal end comprising a tip located thereon, said tip having a length in the range of 0.15 inches (3.8 mm) to 0.23 inches (5.8 mm), and being formed of a second material having a second durometer, said second durometer being substantially lower than said first durometer.

25. An obturator for use within a lumen extending into the body of a living being, said obturator comprising a shaft in the form of an elongated rod-like element having a distal end, said rod-like element being formed of a first material comprising polyurethane and having a first durometer, said distal end comprising a tip located thereon, said tip comprising radiopaque means comprising barium sulfate at a concentration of at least twenty percent by weight of said first material, said tip further comprising a second material comprising polyurethane and having a second durometer, said second durometer being substantially lower than said first durometer.

26. An obturator for use within a lumen extending into the body of a living being, said obturator comprising a shaft in the form of an elongated rod-like element having a distal end, said rod-like element being formed of a first material comprising polyether based polyurethane and having a first durometer, said distal end comprising a tip located thereon, said tip being formed of a second material comprising aliphatic polyurethane having a second durometer and barium sulfate at a concentration of at least twenty percent by weight of said aliphatic polyurethane, said second durometer being substantially lower than said first durometer.

* * * * *